United States Patent [19]

Benoit

[11] Patent Number: 4,572,665
[45] Date of Patent: Feb. 25, 1986

[54] APPARATUS FOR MEASURING THE REFRACTIVE INDEX OF AN OPTICAL FIBER

[75] Inventor: Pierre Benoit, Athenaz, Switzerland

[73] Assignee: Promogap, Geneva, Switzerland

[21] Appl. No.: 550,246

[22] Filed: Nov. 9, 1983

[30] Foreign Application Priority Data

Nov. 15, 1982 [CH] Switzerland ............... 6648/82

[51] Int. Cl.⁴ ............... G01N 21/41; G01N 21/84
[52] U.S. Cl. ............................. 356/73.1; 356/128
[58] Field of Search ........................ 356/73.1, 128

[56] References Cited

U.S. PATENT DOCUMENTS 4,468,118  8/1984  Bice ........................... 356/73.1

FOREIGN PATENT DOCUMENTS 2098352  11/1982  United Kingdom ........... 356/128

OTHER PUBLICATIONS

Saunders, "Optical Fiber Profiles Using the Refracted Near-Field Technique; A Comparison with Other Methods", Applied Optics, vol. 20, No. 9, May 1981, pp. 1645-1651.

Primary Examiner—Vincent P. McGraw
Attorney, Agent, or Firm—Walter H. Schneider

[57] ABSTRACT

The apparatus described basically includes a vessel (10) which has a horizontal transparent window (11) and contains an index liquid (12). An optical fiber (13) is mounted in this vessel perpendicular to the window (11). Light (14) is launched and focused by a condenser (15) onto fiber (13). The light cone of aperture angle ($2\beta$) due to the guided and leaky modes is eliminated using an annular mirror (16) that reflects the remaining portion of the aperture light cone ($2\alpha$) escaping laterally from the fiber. This light reflected by the mirror (16) is focused by an annular condenser (18) and reflected onto a detector (20) by a flat mirror (19) with a hole in the center. Measuring the amount of light received by the detector (20) allows the refractive index of the fiber to be determined.

4 Claims, 6 Drawing Figures

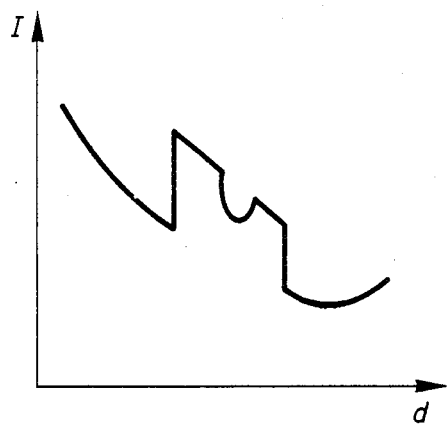
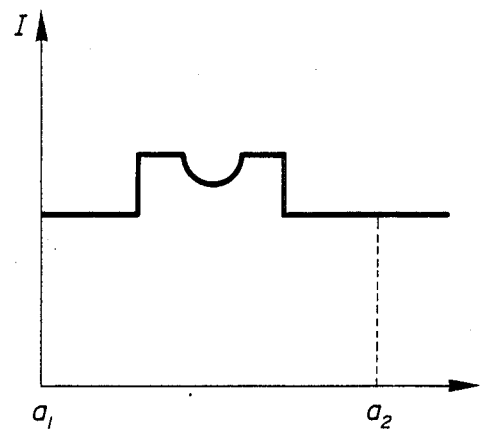
FIG. 3          FIG. 6
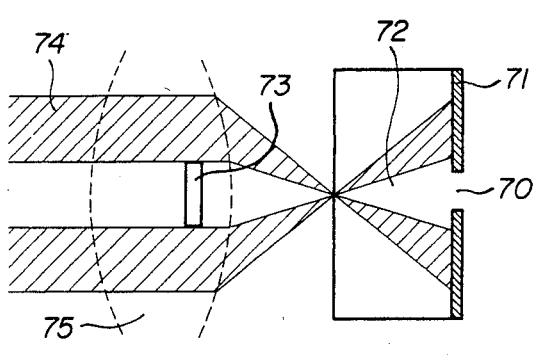
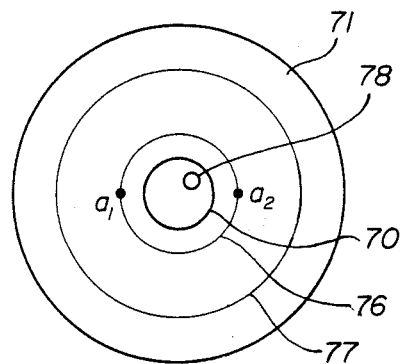
FIG. 4          FIG. 5

APPARATUS FOR MEASURING THE REFRACTIVE INDEX OF AN OPTICAL FIBER

The present invention concerns an apparatus for measuring the refractive index of an optical fiber using the so-called "refracted near-field technique."

Numerous methods for measuring the refractive index of an optical fiber or preform are known, particularly those described in the manual *Principles of optical fiber measurement* by Dietrich Marcuse, published in 1981 by Academic Press. We shall cite for example, the transversal methods applied to preforms and fibers which involve rotation of the fiber or the preform to determine their geometry (eccentricity, ellipticity, diameter, etc.).

We shall also mention interferometric methods which cannot be used in an industrial setting because of sample preparation time, conditions of cleanliness required, etc.

The so-called near-field technique is frequently used. However, leaky modes cannot be eliminated and the measurement must be corrected using approximation formulas.

Another well-known measurement method is the so-called "Fresnel reflection" method which allows high resolution to be attained, but results frequently in measurement errors due to its sensitivity to contamination of the fiber surface being measured.

All these well-known methods which often require complex equipment, skilled labor and careful and complicated preparation of the fiber to be analyzed can, depending on the case, be used in laboratories, but are not suitable for use in industry where working conditions and requirements are totally different. To be used industrially, the apparatus must permit direct reading of the width value measured, and fast and simple preparation and placement of the fiber to be analyzed; a person of average skill should be able to perform these operations.

The present invention proposes to fill this gap by providing an apparatus for measuring the refractive index of a multimode or monomode optical fiber which meets the above-defined conditions for industrial use. The method by which this apparatus operates is the so-called "refracted near-field technique" which is also described in the above-mentioned manual on pages 132 to 141. According to this procedure, light is launched into one end of a multimode or monomode fiber and the amount of light that escapes laterally from this fiber because of the refracted modes is measured. The light cone obtained is filtered using an annular screen which eliminates guided and leaky modes. Direct measurement, after calibration, allows the fefractive index of the fiber to be determined to the thousandth place with an uncertainty of 0.0001 of the value of this index and a spatial resolution of 0.1 to 0.5 μm.

Until now, the device used comprised a vessel of index liquid into which a piece of the fiber end to be analyzed was immersed essentially horizontally, a microscope objective equipped to launch light into this fiber, a screen followed by a lens which focused the light to be measured onto a detector placed on the side of the vessel opposite the microscope. One of the main drawbacks to this arrangement is that the fiber end piece must be guided in such a way that the fiber can cross the side wall of the vessel. To this end, a tube is frequently used, such as, for example, a hypodermic needle inserted in the side wall of the vessel to hold the fiber in the position for measurement. One of the problems posed by this arrangement is, of course, hermeticity of the vessel where the fiber passes through the side wall. Another problem is duplicating the fiber position relative to the focal point of the launch lens. Besides, this relatively delicate arrangement is usable only in a laboratory with certain precautions taken to guarantee that the fiber remains clean and avoid contamination of the vessel and the liquid it contains; it is not suitable for industrial use.

The present invention is intended to remedy this drawback by providing a direct-read apparatus permitting rapid and effective measurement of the refractive index of a mono- or multimode fiber.

To this end, the apparatus according to the invention is characterized by the fact that it comprises a rigid frame holding a vessel that moves in three orthogonal axes and contains an index liquid, and whose bottom includes a horizontal transparent window; a support above the vessel capable of holding the end piece of the fiber to be analyzed perpendicular to the transparent window; a light source and a primary objective to launch a light beam into the optical axis of the fiber via the end held facing the transparent window; a circular screen placed above the vessel to eliminate the light cone formed by the guided and leaky modes; and a detector to catch the remaining parts of the refracted modes of the light cone that escape laterally from the fiber.

The present invention will be better understood by referring to the description of an example of a preferred construction and the attached drawing in which:

FIG. 3 is an intensity variation curve when the beam does not have a constant intensity distribution;

FIG. 4 illustrates a mounting diagram for a mask placed in the parallel beam;

FIG. 5 is a front view illustrating the relative positions of the detector with its central hole and the shadow produced by the mask, and FIG. 6 is the intensity variation curve for an assembly like that shown in FIG. 4.

Figure 1:
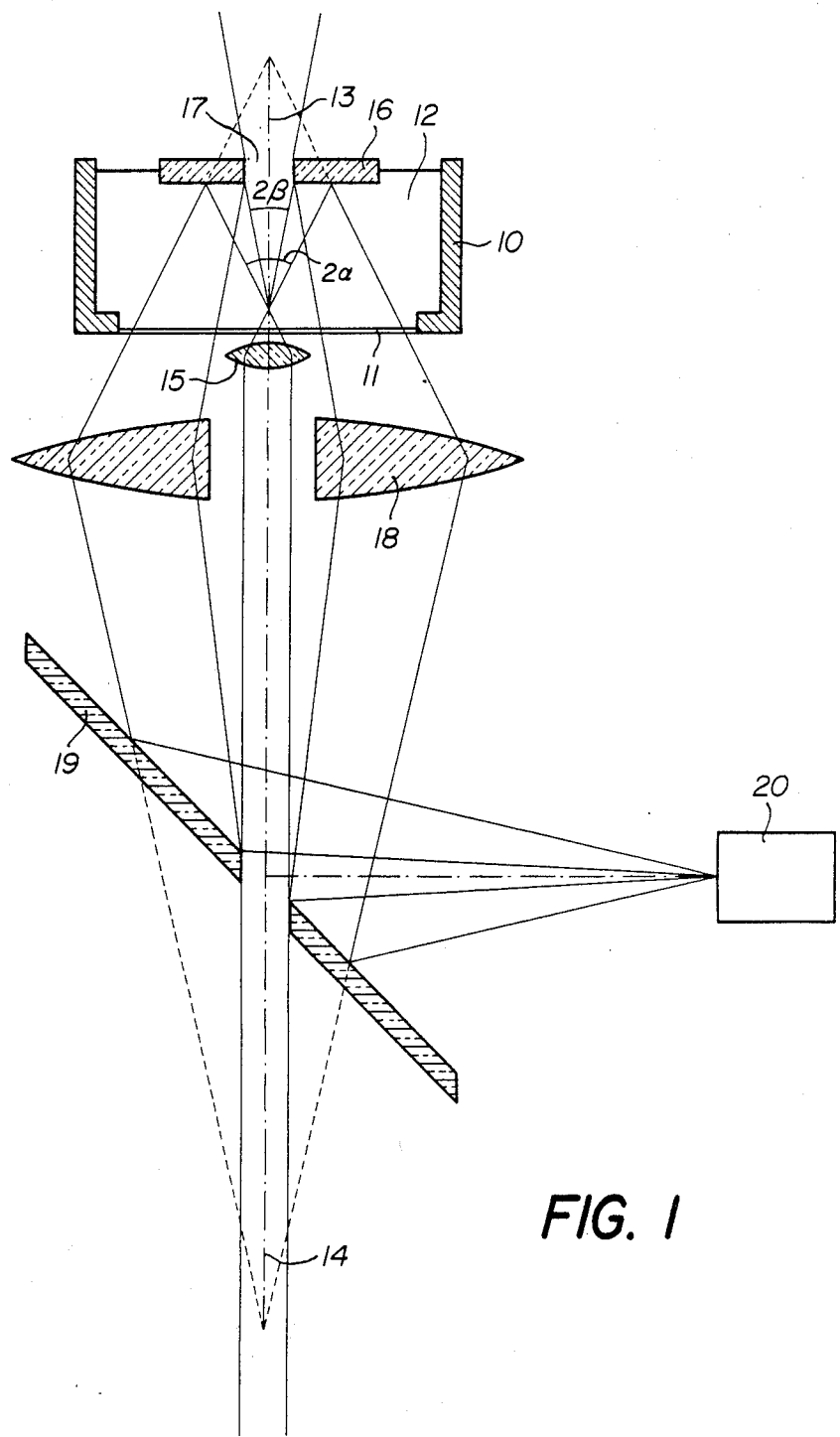
FIG. 1 is a schematic diagram of the apparatus according to the invention for use of the refracted near-field technique to measure the refractive index of an optical fiber.

Referring to FIG. 1, the apparatus described comprises a vessel 10 whose bottom is equipped with a transparent window 11 and which is filled with an index liquid 12. An optical fiber 13, whose refractive index is to be measured, is fixed by support means, not shown, at the center of the vessel in a position essentially perpendicular to the window 11 placed in a horizontal plane.

Light is launched into fiber 13 by means of a light beam 14 focused by a converging lens system under window 11. The light cone of aperture angle $2\alpha$ which escapes laterally from the fiber is partially caught by an annular reflector 16, and depending on the case, by the reflecting side wall of the vessel 10 and partially crosses the central aperture 17 of this reflector. Actually, the light cone is made up of a central cone of aperture angle $2\beta$ that escapes through aperture 17 and represents at least the guided and leaky modes which the above-mentioned method intends to eliminate, and of the portion of the aperture cone $2\alpha$ remaining after the central aperture cone $2\beta$ is eliminated. This remaining light is reflected by reflector 16, focused by annular condenser 18 and reflected by a plane mirror 19 onto a detector 20. As previously mentioned, the measurement of this amount of light allows the refractive index of optical fiber 13 to be determined in an essentially known manner.

This schematic set-up illustrates the operating principles of the apparatus according to the invention. Of course, it is possible to modify this assembly, for example, by eliminating reflector 16 and replacing it with a ring-shaped detector that directly measures the amount of light in the remaining portion of the light cone of angle 2α when the center portion relative to the guided and leaky modes was filtered by the round center aperture of the detector. Another possibility consists of replacing the central aperture with a circular screen for the purpose of eliminating at least the leaky and guided modes. In these different cases, the diameter of the central aperture or that of the screen is at least sufficient to guarantee total elimination of the leaky and guided modes, that is, at least equal to the diameter of the circle of intersection of the cone formed by the guided and leaky modes and the plane of the detector or reflector and/or the screen.

Figure 2:
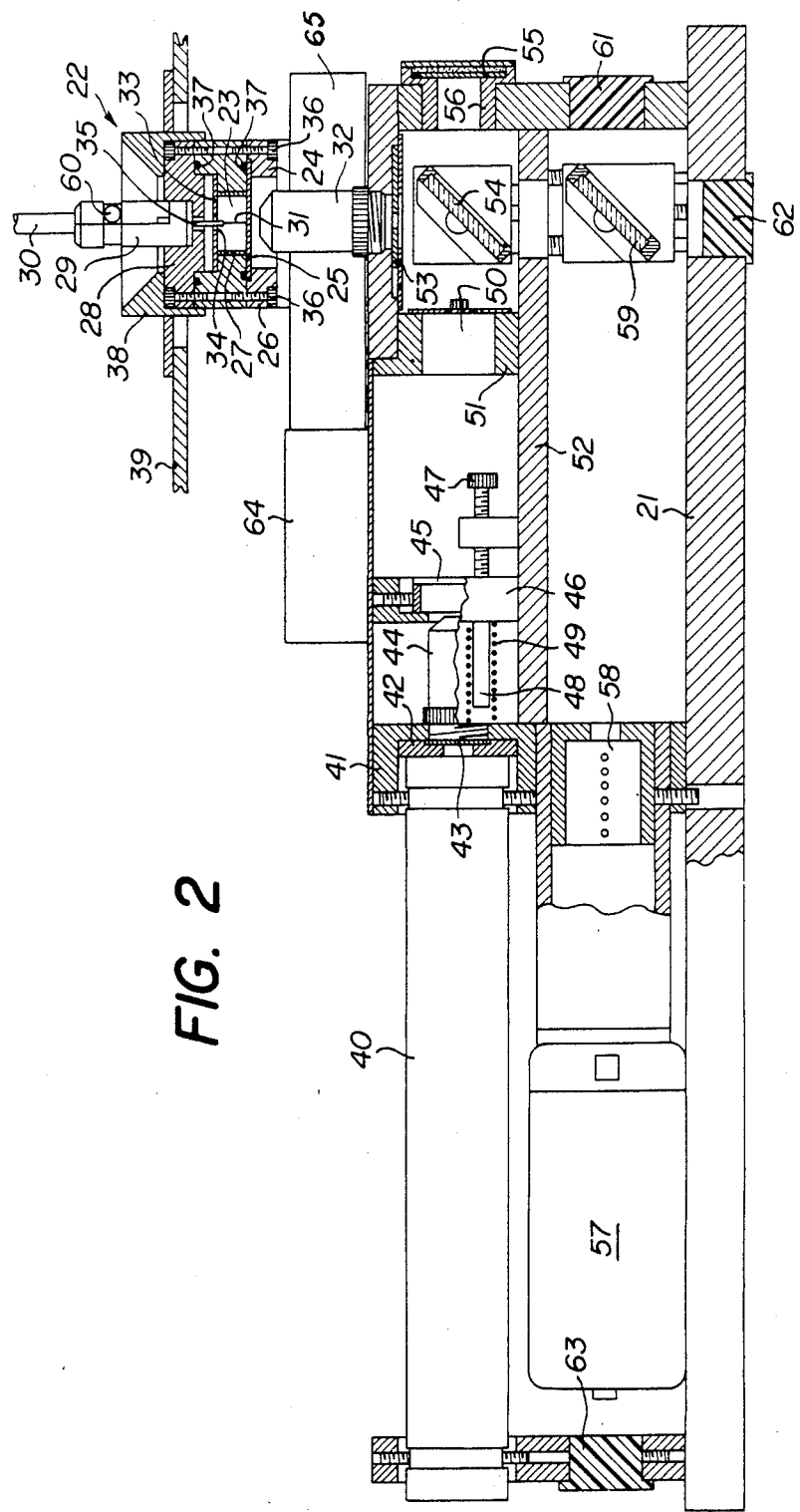
FIG. 2 is an axial cut-away view of the preferred construction of the apparatus according to the invention.

FIG. 2 illustrates the preferred embodiment of the apparatus represented schematically in FIG. 1. This apparatus is basically composed of a bed 21 on which the different components described in the reference to FIG. 1 are mounted. First, measurement cell 22 comprises a vessel 23 filled with an index liquid and is formed basically of a base block 24 that supports a transparent window 25 forming the bottom of the vessel, of a block 26 forming the side walls of vessel 23 or at least supporting a cylindrical jacket 27 which acts as the side walls of this vessel, and of an upper block 28 which covers the measuring cell 22. The side walls of block 26 or of jacket 27 can be reflective to permit the use of a wide-aperture launch lens. Upper block 28 holds a support 29, provided for mounting and securing an optical cable 30 whose naked end 31 is inside vessel 23 and placed on the vertical axis defining the optical axis of objective 32, which is intended to launch light into the fiber and placed under window 25. A ring-shaped detector 33 covers vessel 23, or more exactly, is immersed inside this vessel, resting on an annular flange place in central block 26. This detector has a central aperture 34 whose diameter is equal to the intersection of the plane of this detector with the light cone produced by the leaky modes (aperture angle 2β in the device in FIG. 1). The diameter of this aperture is sufficient to allow passage of the fiber and possibly its support. This aperture can also function as a screen used in the conventional embodiment of the above-mentioned method. A tube 35 to guide and secure the naked end 31 of the optical fiber in cable 30 is inserted through said central aperture 34 of detector 33.

The three blocks 24, 26, and 28, which support vessel 23, are assembled using packing bolts 36. Hermeticity between these blocks is ensured by ring seals 37. A protective cowl 38 is mounted at the top end of the measurement cell 22. A cover 39 (partially illustrated) covers and protects the essential components of the apparatus shown.

In this particular construction, the light source is a laser 40 mounted on support plate 41 against a ring-shaped brace 42. A quarter-wave plate 43 and objective 44 are attached to support 41 in front of laser 40. A plate 45 having a center pinhole is placed in front of the objective and is mounted in a known method onto support 46, whose position is adjustable.

To permit this adjustment, support 46 comprises an adjustment screw 47 and two axial rods 48 cooperating with two coil springs 49 engaged on these rods. A lens 50 at the exit from the spatial filter is mounted on bracket 51, attached to support 52 holding the light source and its various additional components.

At the intersection of the respective optical axes of laser 40 and objective 32, provided with an adjustable diaphragm 53, a semireflecting apparatus 54 is set at 45° to the two above-mentioned optical axes; this semireflecting apparatus can be a separator mirror or preferably a selective mirror of the laser mirror type. This mirror reflects about 99% of the incident light beam through objective 32 onto the end of fiber 31 and transmits about 1% of the nonreflected light onto a reference detector 55 placed at least approximately on the optical axis. The purpose of this detector is to monitor the stability of the light source. Preferably, it is mounted on a tubular support 56 housed in a suitable bore provided in the bed.

To monitor the operation of the apparatus more effectively, it preferably has a television camera 57 mounted on the bed and equipped with an objective 58. The optical axis of this objective is essentially parallel to the optical axis of the laser and the lens system associated with it. A mirror 59 tilted at 45° to the horizontal is placed at the intersection of the optical axes of the television camera objective 58 and objective 32. To display the fiber, support 29 of the optical cable 30 is equipped with a device 60 allowing light, for example, blue light with a wavelength different from that of the laser beam, to be launched laterally into the optical fiber. This light emitted via the end of the optical fiber is sent by selective mirror 54 and reflected by mirror 59 onto objective 58 of television camera 57.

To permit adjustment of the device, plugs 61, 62 and 63 are placed on the path of the light rays and are set into appropriate cavities provided for them in the bed.

Blocks 64 and 65 represent motorized units, comprising small motors (not shown) that move the measuring cell 22 as desired along axes X, Y and Z of the previously mentioned orthogonal reference system.

By scanning in the X, Y plane, the apparatus described above allows determination of the index profile, geometry and particularly its eccentricity to be determined with a space resolution on the order of 0.1 to 0.5 $\mu$m. In addition, it has the advantage of determining monomode fiber characteristics.

Of course, different optical components considered standard in this assembly can be replaced by equivalent optical components. For example, plane mirror 16 and annular condenser 18 illustrated in FIG. 1 can be replaced by a concave annular reflector to focus reflected beams onto detector 20.

In these embodiments, the central aperture, which acts as a screen interposed in the light beam to eliminate the light cone formed by the guided and leaky modes, is moved laterally relative to the beam when the detector moves. If the beam does not have a constant intensity distribution, the level of the intensity detected varies according to a curve shown in FIG. 3 where the intensity I is given on the y-axis and the lateral displacement of the detector relative to the beam axis is given on the x-axis.

To eliminate this drawback, it is proposed to mount a central mask in the parallel beam; this mask is designed in such a way that its projected shadow completely covers the central aperture of the detector. The diameter of the shadow is preferably greater than the diameter of the detector aperture.

FIG. 4 is a schematic illustration of the preferred position of the mask mounted in the objective for centering purposes and placed parallel in the beam for construction purposes. The central aperture 70 of detector 71 has a diameter less than the area of shadow projected by shadow cone 72 produced by circular mask 73 placed in the parallel beam 74 and mounted in the microscope objective 75.

FIG. 5 is a front view illustrating the relative positions of the detector 71, the center hole 70 of this detector, the projected area of shadow 76, luminous area 77 and passage hole 78 of the optical fiber.

As shown particularly in FIG. 6, light intensity in the measurement zone defined by segment $a_1a_2$ varies according to the graph shown. The level of this intensity remains constant, as in conventional systems in which the detection-collection screen is fixed in relation to the beam.

I claim:

1. In an apparatus for measuring the refractive index of an optical fiber using the "refracted near-field technique" comprising a rigid frame supporting a vessel adapted to move along three orthogonal axes, said vessel being further adapted to hold an index liquid and having a bottom provided with a horizontally disposed transparent window; means above said vessel for supporting a fiber to be analyzed and for positioning said fiber with an end thereof adjacent and perpendicular to said transparent window; a light source in combination with a primary optical device for directing a light beam along the optical axis of said fiber through its end adjacent said transparent window; means for eliminating the portion of the resulting light cone representing guided and leaky modes; and a detector for measuring the portion of the light cone representing the remaining modes, the improvement in which said detector is annular-shaped having its annulus coaxial with said fiber end and with at least the surface thereof facing the directed light beam being immersed in the index fluid in said vessel, said annulus comprising said means for eliminating the portion of the light cone representing guided and leaky modes.

2. In an apparatus for measuring the refractive index of an optical fiber using the "refracted near-field technique" comprising a rigid frame supporting a vessel adapted to move along three orthogonal axes, said vessel being further adapted to hold an index fluid and having a bottom provided with a horizontally disposed transparent window; means above said vessel for supporting a fiber to be analyzed and for positioning said fiber with an end thereof adjacent and perpendicular to said transparent window; a light source in combination with a primary optical device for directing a light beam along the optical axis of said fiber through its end adjacent said transparent window; and means for eliminating the portion of the resulting light cone representing guided and leaky modes and for intercepting the portion of the light cone representing the remaining modes and transmitting it to a detector, the improvement in which said eliminating and intercepting means comprises an annular-shaped plane mirror having its annulus coaxial with said fiber end and with at least the surface thereof facing the directed light beam being immersed in the fluid in said vessel, said annulus effecting the elimination of the light cone representing guided and leaky modes and said mirror effecting the interception of the portion of the light cone representing the remaining modes and transmitting it to a detector located on the same side of said vessel as said light source.

3. The improvement according to claim 2 in which an annular-shaped converging lens having its annulus coaxial with said fiber end is placed between said plane mirror and said detector for focusing the portion of the light cone representing the remaining modes on said detector, the light beam originating with said light source being directed through the annulus of said lens.

4. The improvement according to claim 3 in which a second annular-shaped plane mirror is placed between said light source and said annular-shaped converging lens for reflecting to said detector the portion of the light cone representing the remaining modes, the light beam originating with said light source being directed through the annulus of said second annular-shaped plane mirror.

* * * * *